United States Patent
Dubief et al.

(10) Patent No.: US 7,476,393 B2
(45) Date of Patent: Jan. 13, 2009

(54) PROCESS FOR THE PREPARATION OF A CATIONIC NANOEMULSION, AND COSMETIC COMPOSITION

(75) Inventors: Claude Dubief, Le Chesnay (FR); Geraldine Fack, Levallois (FR); Luc Nicolas-Morgantini, Rully (FR); Serge Restle, Saint-Prix (FR)

(73) Assignee: L'Oreal, Paris (FR)

( * ) Notice: Subject to any disclaimer, the term of this patent is extended or adjusted under 35 U.S.C. 154(b) by 904 days.

(21) Appl. No.: 10/717,626

(22) Filed: Nov. 21, 2003

(65) Prior Publication Data

US 2004/0151746 A1  Aug. 5, 2004

Related U.S. Application Data

(60) Provisional application No. 60/432,635, filed on Dec. 12, 2002.

(30) Foreign Application Priority Data

Nov. 29, 2002  (FR) .................................. 02 15080

(51) Int. Cl.
*A61Q 5/00* (2006.01)
*A61K 8/06* (2006.01)

(52) U.S. Cl. .................. 424/401; 424/70.1; 424/70.19; 424/70.27; 424/70.28; 424/70.31

(58) Field of Classification Search .................. 424/401
See application file for complete search history.

(56) References Cited

U.S. PATENT DOCUMENTS

| 5,298,240 | A | 3/1994 | Schroeder et al. |
| 5,468,725 | A | 11/1995 | Guenin et al. |
| 2001/0028887 | A1 | 10/2001 | Douin et al. |
| 2002/0098215 | A1 | 7/2002 | Douin et al. |

FOREIGN PATENT DOCUMENTS

| DE | 197 10 155 | 9/1998 |
| EP | 0 820 758 | 1/1998 |
| EP | 1 120 102 | 8/2001 |
| EP | 1 129 684 | 9/2001 |
| WO | 01/56537 | 8/2001 |
| WO | WO 01/56537 A1 * | 8/2001 |

* cited by examiner

*Primary Examiner*—Sreeni Padmanabhan
*Assistant Examiner*—Sahar Javanmard
(74) *Attorney, Agent, or Firm*—Oblon, Spivak, McClelland, Maier & Neustadt, P.C.

(57) ABSTRACT

The present invention relates to a process for the preparation of a cationic nanoemulsion, to a cosmetic composition obtainable by said process and to the use of said composition.

28 Claims, 1 Drawing Sheet

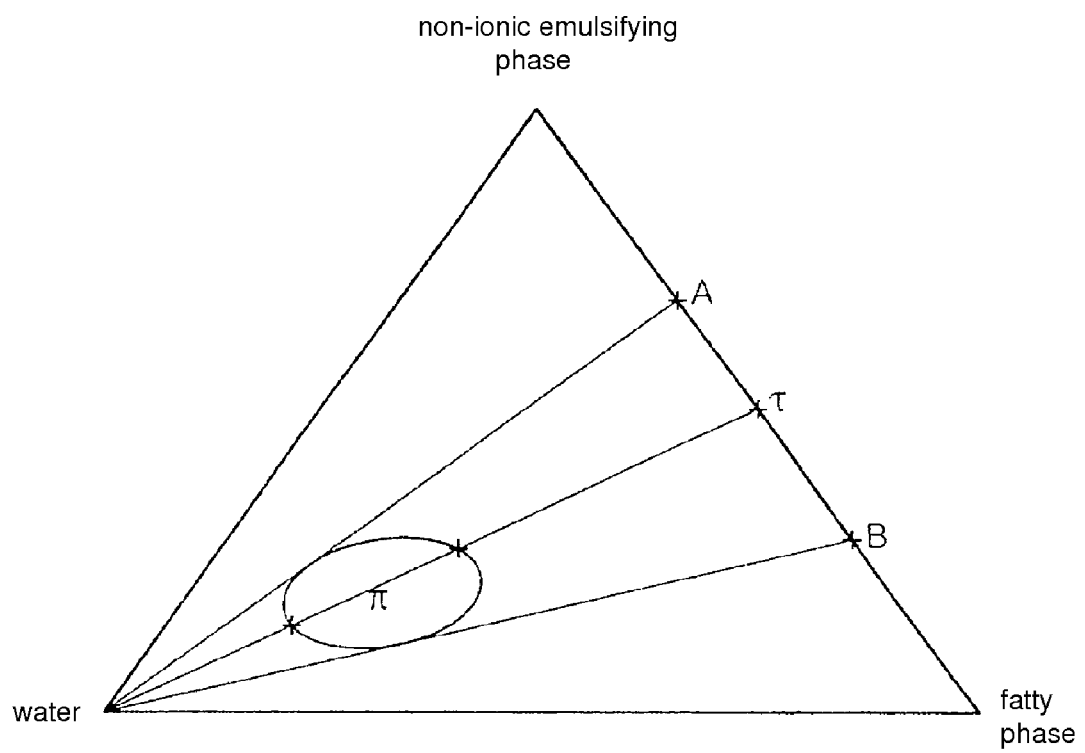

PROCESS FOR THE PREPARATION OF A CATIONIC NANOEMULSION, AND COSMETIC COMPOSITION

BACKGROUND OF THE INVENTION

1. Field of the Invention

The present invention relates to a process for the preparation of a cationic nanoemulsion, to a cosmetic composition obtainable by said process and to the use of said composition.

2. Discussion of the Background

The microemulsions and nanoemulsions of the prior art are well known in cosmetics and are sought for their cosmetic properties. They make it possible in particular to obtain a disentangling effect, softness, a feel, rinsability and a conditioning effect on keratin materials, such as hair, which are better than those obtained with the conventional emulsions and dispersions used in this field.

Microemulsions and nanoemulsions are generally obtained either by a high pressure homogenization process or by a phase inversion temperature process. However, these two processes exhibit major disadvantages.

In fact, the high pressure homogenization process requires specific and particularly extensive equipment to be able to work under substantial pressures ranging from $12.10^7$ to $18.10^7$ Pa, so this process is not easy to carry out in industry.

The phase inversion temperature process (or PIT process) yields nanoemulsions whose particle size is rarely below 100 nm.

SUMMARY OF THE INVENTION

The Applicant has now discovered, surprisingly, that by successively mixing, with agitation, the components of the fatty phase and non-ionic surfactants, at a temperature above the melting points of the components of the fatty phase and the non-ionic surfactants, and under normal atmospheric pressure, and then water, followed by the addition of at least one cationic surfactant, cationic nanoemulsions of the oil-in-water type are obtained which have a number-average particle size below 100 nm.

These cationic nanoemulsions obtained by this process also have cosmetic properties, such as a disentangling effect, a softness, a feel, a rinsability and a conditioning effect, which are appreciably better than the cosmetic properties of the nanoemulsions of the prior art.

This process is also easier to carry out than the two known processes of the prior art mentioned above, and do not require specific equipment.

The present invention therefore relates to a process for the preparation of a cationic nanoemulsion.

The invention further relates to a cosmetic composition in the form of a cationic nanoemulsion obtainable by said process.

The invention further relates to the use of said composition as a cleaning, dyeing or perming composition or as a treatment composition before or after dyeing, perming, bleaching or straightening.

The invention further relates to a method of treating keratin materials using said composition.

Other objects, characteristics, features and advantages of the invention will become even more clearly apparent on reading the description and the various examples which follow.

BRIEF DESCRIPTION OF THE DRAWINGS

FIG. 1 A ternary phase diagram of fatty phase, non-ionic emulsifying phase, and water for the determination of the zone in which a nanoemulsion of the oil-in-water type is formed.

DETAILED DESCRIPTION OF THE INVENTION

According to the invention, the process for the preparation of a cationic nanoemulsion comprises the following steps:

(a) mixing, with agitation, of at least one fatty compound and at least one non-ionic surfactant, preferably at least two non-ionic surfactants, at a temperature $T_m$ above the melting point of the fatty compound(s) and the non-ionic surfactant(s), under normal atmospheric pressure, the ternary phase diagram fatty compound(s)/non-ionic surfactant(s)/water exhibiting at least one zone where a nanoemulsion phase of the oil-in-water type exists, and the concentrations of the fatty compound(s) and the non-ionic surfactant(s) being chosen so that this nanoemulsion zone can be reached simply by dilution with water, (b) addition of water, with agitation, so as to reach this nanoemulsion zone, and (c) addition of at least one cationic surfactant to the resulting nanoemulsion.

As used herein, "normal pressure" means standard pressure as known in the art, i.e., 1 atm at sea level.

The choice of proportions of the components of the nanoemulsion is therefore made on the basis of the ternary phase diagram fatty phase/non-ionic emulsifying phase/water, in which the fatty phase consists of at least one fatty compound such as described below and the non-ionic emulsifying phase consists of at least one non-ionic surfactant such as described below. This diagram makes it possible to determine the zone in which a nanoemulsion of the oil-in-water type is formed. Such a diagram is shown in FIG. 1, where p represents the formation zone of said nanoemulsion.

Once the ternary phase diagram has been plotted by techniques well known to those skilled in the art, the proportions of the emulsifying phase and the fatty phase are chosen so that the weight ratio τ of fatty compound(s) to non-ionic surfactant(s) is between A and B, these points being shown in FIG. 1.

This weight ratio τ is generally below 2, preferably between 0.1 and 1.5 and better still between 0.1 and 1.

The temperature $T_m$ is preferably between room temperature and 100° C. and better still between 20° C. and 85° C. Room temperature is understood to mean a temperature of about 20° C.

Water is preferably added at around the temperature $T_m$ and particularly preferably at a temperature Θ of between $T_m$ and $T_m-20°$ C.

The amount of fatty compound(s) used in step (a) is generally between 1 and 30% by weight, preferably between 1 and 20% by weight, preferably between 2 and 15% by weight and particularly preferably between 4 and 12% by weight, based on the total weight of the cationic nanoemulsion.

The amount of non-ionic surfactant(s) used in step (a) is generally between 2 and 30% by weight, preferably between 2 and 20% by weight and particularly preferably between 8 and 20% by weight, based on the total weight of the cationic nanoemulsion.

The amount of water generally added in step (b) of the process is between 40 and 97% by weight and preferably between 50 and 90% by weight, more preferably between 65 and 90% by weight based on the total weight of the cationic nanoemulsion.

When the nanoemulsion has been obtained, at least one cationic surfactant is added. The cationic surfactant added is preferably in the form of an aqueous solution or dispersion. The temperature at which the cationic surfactant is added is not critical, but the chosen temperature will preferably be close to Θ or $T_m$.

The amount of cationic surfactant(s) used in step (c) is generally between 0.1 and 10% by weight and preferably between 0.2 and 6% by weight, based on the total weight of the cationic nanoemulsion.

The phase for cooling to room temperature can take place before or after step (c). In both cases, the particle size is preserved during this cooling, which notably is not the case in a PIT process.

The process according to the invention affords a nanoemulsion whose particles have a number-average size below 100 nm, preferably of between 10 and 100 nm and particularly preferably of between 20 and 90 nm.

The number-average particle size can be determined in particular by the known method of quasi-elastic light scattering. One apparatus that can be used for this determination is the BROOKHAVEN apparatus equipped with an SX 200 optical bench (with 532 nm laser) and a BI 9000 correlator. This apparatus provides a measure of the mean diameter by photon correlation spectroscopy (or PCS), which makes it possible to determine the number-average diameter from the polydispersity factor, which is also measured by the apparatus.

The nanoemulsion can also be characterized by measurement of its turbidity by the NTU method using a HACH 2100P turbidimeter at room temperature. The turbidity of the nanoemulsions of the invention is generally below 400 NTU and preferably between 50 and 250 NTU.

The fatty compounds which can be used in the process according to the invention are preferably selected from fatty acid esters, transesterified or non-transesterified vegetable oils, and mixtures thereof.

Fatty acid esters which may be mentioned in particular are the compounds of the formula $R_aCOOR_b$, in which $R_a$ is the radical of a saturated or unsaturated fatty acid containing from 6 to 29 carbon atoms and preferably from 8 to 22 carbon atoms, and $R_b$ is a saturated or unsaturated hydrocarbon chain containing from 1 to 30 carbon atoms and preferably from 1 to 12 carbon atoms, such as purcellin oil (stearyl octanoate), isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate or 2-octyldodecyl myristate or lactate.

Vegetable oils which may be mentioned in particular are sweet-almond oil, avocado oil, castor oil, olive oil, jojoba wax, sunflower oil, wheatgerm oil, sesame oil, groundnut oil, grape seed oil, soya oil, colza oil, safflower oil, copra oil, maize oil, hazelnut oil, shea butter, palm oil, apricot kernel oil and calophyllum oil.

The transesterified vegetable oil used is preferably olive oil transesterified with hexanol or jojoba wax transesterified with ethanol.

The fatty compounds that are particularly preferred within the framework of the present invention are isopropyl myristate, isononyl isononanoate, jojoba wax, olive oil transesterified with hexanol, jojoba wax transesterified with ethanol, and mixtures thereof.

The non-ionic surfactants which can be used in the process of the invention are also compounds well known per se (cf. particularly "Handbook of Surfactants" by M. R. PORTER, published by Blackie & Son (Glasgow and London), 1991, pp 116-178). Thus they can be chosen especially from (non-limiting list) polyalkoxylated (2-50 mol of alkylene oxide), preferably polyethoxylated or polypropoxylated, hydrogenated or non-hydrogenated vegetable oils, $C_{8-30}$ fatty acid mono-, di- or triglycerides, polyethoxylated and/or polypropoxylated alcohols, polyethoxylated and/or polypropoxylated alpha-diols, polyethoxylated and/or polypropoxylated alkylphenols having a fatty chain containing e.g. 8 to 18 carbon atoms, it being possible for the number of ethylene oxide or propylene oxide groups to range from 2 to 50 in particular, and mixtures thereof. The following may also be mentioned: ethylene oxide/propylene oxide copolymers, condensation products of ethylene oxide and propylene oxide with fatty alcohols; polyethoxylated fatty amides having preferably from 2 to 30 mol of ethylene oxide, polyglycerolated fatty amides containing an average of 1 to 5 and particularly 1.5 to 4 glycerol groups; fatty acid esters of sorbitan or polyethoxylated fatty acid esters of sorbitan having from 2 to 30 mol of ethylene oxide; fatty acid esters of sucrose, fatty acid esters, preferably $C_{8-30}$ fatty acid esters, of polyethylene glycol, $C_{8-30}$ fatty acid esters of polyglycerol, alkylpolyglycosides, N-alkylglucamine derivatives and amine oxides, such as $(C_{10}-C_{14}$-alkyl)amine oxides or N-acylaminopropylmorpholine oxides.

The non-ionic surfactants which are particularly preferred in the invention are selected especially from polyethoxylated hydrogenated castor oil containing 35 mol of ethylene oxide (hereafter referred to as "with 35 EO"), polyethoxylated hydrogenated castor oil containing 7 mol of ethylene oxide (or with 7 EO), polyethoxylated olive oil with 7 EO, sorbitan monooleates with 4 EO, 5 EO or 20 EO, $(C_{12}-C_{14}$-alkyl) glycosides or $(C_8-C_{14}$-alkyl)glycosides, glycerol monostearate with 30 EO, decaglyceryl monooleate, polyalkoxylated oleyl alcohol with 2 or 10 EO, polyethoxylated lauryl alcohol with 7 EO, methylglucoside dioleate, and mixtures thereof.

The cationic surfactants which can be used in the process according to the invention are those well known per se, such as salts of optionally polyalkoxylated primary, secondary or tertiary fatty amines, quaternary ammonium salts and mixtures thereof.

More particularly preferred cationic surfactants are quaternary ammonium salts, for example:

those of general formula (I) below:

(I)

in which the radicals $R_1$ to $R_4$, which can be identical or different, are a linear or branched aliphatic radical containing from 1 to 30 carbon atoms or an aromatic radical such as aryl or alkylaryl. The aliphatic radicals can contain heteroatoms such as, in particular, oxygen, nitrogen, sulphur and halogens. The aliphatic radicals are selected e.g. from alkyl, alkoxy, polyoxyalkylene oxide ($C_2-C_6$), alkylamide, alkyl($C_{12}-C_{22}$) amidoalkyl($C_2-C_6$), alkyl($C_{12}-C_{22}$) acetate and hydroxyalkyl radicals containing from about 1 to 30 carbon atoms; X is an anion selected from the group comprising halides, phosphates, acetates, lactates, alkyl($C_1-C_6$)sulphates, ($C_1-C_6$-alkyl)sulphonates and ($C_1-C_6$-alkyl)arylsulphonates;

quaternary ammonium salts of imidazoline, for example those of formula (II) below:

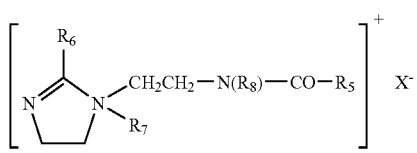

in which $R_5$ is an alkenyl or alkyl radical containing from 8 to 30 carbon atoms derived e.g. from tallow fatty acids, $R_6$ is a hydrogen atom, a $C_1$-$C_4$-alkyl radical or an alkenyl or alkyl radical containing from 8 to 30 carbon atoms, $R_7$ is a $C_1$-$C_4$-alkyl radical, $R_8$ is a hydrogen atom or a $C_1$-$C_4$-alkyl radical and $X^-$ is an anion selected from the group comprising halides, phosphates, acetates, lactates, alkylsulphates, alkylsulphonates and alkylarylsulphonates. Preferably, $R_5$ and $R_6$ are a mixture of alkenyl or alkyl radicals containing from 12 to 21 carbon atoms derived e.g. from tallow fatty acids, $R_7$ is a methyl radical and $R_8$ is a hydrogen atom. Such a product is marketed e.g. under the name REWOQUAT® W 75 by REWO;

the quaternary diammonium salts of formula (III):

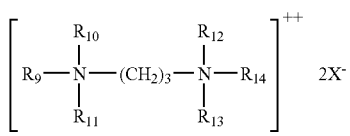

in which $R_9$ is an aliphatic radical containing approximately from 16 to 30 carbon atoms, $R_{10}$, $R_{11}$, $R_{12}$, $R_{13}$ and $R_{14}$, which are identical or different, are selected from hydrogen and an alkyl radical containing from 1 to 4 carbon atoms, and X is an anion selected from the group comprising halides, acetates, phosphates, nitrates and methylsulphates. Such quaternary diammonium salts include propanetallow-diammonium dichloride in particular; and quaternary ammonium salts containing at least one ester group, such as those of formula (IV) below:

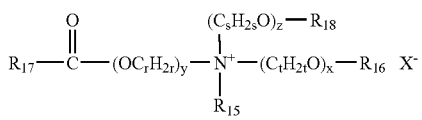

in which:

$R_{15}$ is selected from $C_1$-$C_6$-alkyl radicals and $C_1$-$C_6$-hydroxyalkyl or $C_1$-$C_6$-dihydroxyalkyl radicals;

$R_{16}$ is selected from:
the radical

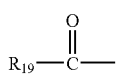

saturated or unsaturated, linear or branched $C_1$-$C_{22}$ hydrocarbon radicals $R_{20}$, and
the hydrogen atom;

$R_{18}$ is selected from:
the radical

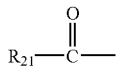

saturated or unsaturated, linear or branched $C_1$-$C_6$ hydrocarbon radicals $R_{22}$, and
the hydrogen atom;

$R_{17}$, $R_{19}$ and $R_{21}$, which are identical or different, are selected from saturated or unsaturated, linear or branched $C_7$-$C_{21}$, hydrocarbon radicals;

r, s and t, which are identical or different, are integers with values of 2 to 6;

y is an integer with a value of 1 to 10;

x and z, which are identical or different, are integers with values of 0 to 10; and $X^-$ is a simple or complex organic or inorganic anion;

with the proviso that the sum x+y+z has a value of 1 to 15, that when x has a value of 0, $R_{16}$ is $R_{20}$, and that when z has a value of 0, $R_{18}$ is $R_{22}$.

The alkyl radicals $R_{15}$ can be linear or branched and more particularly linear.

$R_{15}$ is preferably a methyl, ethyl, hydroxyethyl or dihydroxypropyl radical and more particularly a methyl or ethyl radical.

The sum x+y+z advantageously has a value of 1 to 10.

If $R_{16}$ is a hydrocarbon radical $R_{20}$, it can be long and have from 12 to 22 carbon atoms or it can be short and have from 1 to 3 carbon atoms.

If $R_{18}$ is a hydrocarbon radical $R_{22}$, it preferably has 1 to 3 carbon atoms.

Advantageously, $R_{17}$, $R_{19}$ and $R_{21}$, which are identical or different, are selected from saturated or unsaturated, linear or branched $C_{11}$-$C_{21}$ hydrocarbon radicals and more particularly from saturated or unsaturated, linear or branched $C_{11}$-$C_{21}$-alkyl and $C_{11}$-$C_{21}$-alkenyl radicals.

x and z, which are identical or different, preferably have values of 0 or 1.

y is advantageously equal to 1.

r, s and t, which are identical or different, preferably have values of 2 or 3 and more particularly are equal to 2.

The anion is preferably a halide (chloride, bromide or iodide) or an alkylsulphate, more particularly methylsulphate, but it is possible to use methanesulphonate, phosphate, nitrate, tosylate, an anion derived from an organic acid, such as acetate or lactate, or any other anion compatible with ammonium carrying an ester group.

The anion $X^-$ is more particularly chloride or methylsulphate.

The ammonium salts of formula (IV) which are used more particularly in the composition according to the invention are those in which:

$R_{15}$ is a methyl or ethyl radical;
x and y are equal to 1;
z is equal to 0 or 1;
r, s and t are equal to 2;
$R_{16}$ is selected from:
the radical

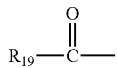

methyl, ethyl or $C_{14}$-$C_{22}$ hydrocarbon radicals, and the hydrogen atom;

$R_{18}$ is selected from:

the radical

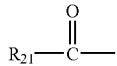

and the hydrogen atom;

$R_{17}$, $R_{19}$ and $R_{21}$, which are identical or different, are selected from saturated or unsaturated, linear or branched $C_{13}$-$C_{17}$ hydrocarbon radicals and preferably from saturated or unsaturated, linear or branched $C_{13}$-$C_{17}$-alkyl and $C_{13}$-$C_{17}$-alkenyl radicals.

The hydrocarbon radicals are advantageously linear.

Examples which may be mentioned are compounds of formula (IV) such as salts (especially chloride or methylsulphate) of diacyloxyethyldimethylammonium, diacyloxyethylhydroxyethylmethylammonium, monoacyloxyethyldihydroxyethylmethylammonium, triacyloxyethylmethylammonium, monoacyloxyethylhydroxyethyldimethylammonium and mixtures thereof. The acyl radicals preferably have 14 to 18 carbon atoms and originate more particularly from a vegetable oil such as palm or sunflower oil. If the compound contains several acyl radicals, these can be identical or different.

These products are obtained e.g. by the direct esterification of optionally alkoxylated triethanolamine, triisopropanolamine, alkyldiethanolamine or alkyldiisopropanolamine with fatty acids or with mixtures of fatty acids of vegetable or animal origin, or by the transesterification of their methyl esters. This esterification is followed by quaternization with an alkylating agent such as an alkyl (preferably methyl or ethyl) halide, a dialkyl (preferably dimethyl or diethyl)sulphate, methyl methanesulphonate, methyl paratoluenesulphonate, glycol chlorohydrin or glycerol chlorohydrin.

Such compounds are marketed e.g. under the names DEHYQUART® by HENKEL, STEPANQUAT® by STEPAN, NOXAMIUM® by CECA and REWOQUAT® WE 18 by REWO-WITCO.

An example of a mixture of ammonium salts which can be used is a mixture containing 15 to 30% by weight of acyloxyethyldihydroxyethylmethylammmonium methylsulphate, 45 to 60% of diacyloxyethylhydroxyethylmethylammonium methylsulphate and 15 to 30% of triacyloxyethylmethylammonium methylsulphate, the acyl radicals having from 14 to 18 carbon atoms and originating from optionally partially hydrogenated palm oil.

It is also possible to use the ammonium salts containing at least one ester group which are described in patents U.S. Pat. Nos. 4,874,554 and 4,137,180.

Preferred quaternary ammonium salts of formula (I) are on the one hand tetraalkylammonium chlorides, for example dialkyldimethylammonium or alkyltrimethylammonium chlorides in which the alkyl radical contains approximately from 12 to 22 carbon atoms, particularly behenyltrimethylammonium chloride (Genamin® KDMP from Clariant) and distearyldimethylammonium, cetyltrimethylammonium and benzyldimethylstearylammonium chlorides, and on the other hand palmitylamidopropyltrimethylammonium chloride or stearamidopropyldimethyl(myristyl acetate)ammonium chloride marketed under the name CERAPHYL® 70 by VAN DYK.

The particularly preferred cationic surfactants in the process of the invention are selected from quaternary ammonium salts and in particular from palmitylamidopropyltrimethylammonium chloride, cetyltrimethylammonium chloride and behenyltrimethylammonium chloride.

The present invention further relates to a cosmetic composition in the form of a cationic nanoemulsion of the oil-in-water type whose particles have a number-average size below 100 nm, preferably of between 10 and 100 nm and particularly preferably of between 20 and 90 nm. It comprises at least one fatty compound, at least one and preferably at least two non-ionic surfactants in an amount of 2 to 30% by weight, at least one cationic surfactant, all as described above, and water, in proportions such that the weight ratio τ of fatty compound(s) to non-ionic surfactant(s) is from 0.1 to 1.5 and particularly preferably from 0.1 to 1, Said cationic surfactant is selected from:

those of general formula (V) below:

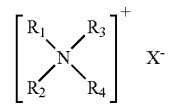

in which the radical R1 is a linear or branched aliphatic radical containing from 8 to 30 carbon atoms or an aromatic radical such as aryl or alkylaryl, the radicals $R_2$ to $R_4$, which can be identical or different, are a linear or branched aliphatic radical containing from 1 to 6 carbon atoms, in particular alkyl ou hydroxyalkyl; and X is an anion selected from the group comprising halides, phosphates, acetates, lactates, alkyl($C_1$-$C_6$)sulphates, ($C_1$-$C_6$-alkyl)sulphonates and ($C_1$-$C_6$-alkyl)arylsulphonates;

The aliphatic radicals R1 can contain heteroatoms such as, in particular, oxygen, nitrogen, sulphur and halogens. The aliphatic radicals are selected e.g. from alkyl, alkoxy, ($C_2$-$C_6$), alkylamide, alkyl($C_{12}$-$C_{22}$)amidoalkyl($C_2$-$C_6$), alkyl ($C_{12}$-$C_{22}$) acetate and hydroxyalkyl radicals containing from about 8 to 30 carbon atoms;

quaternary ammonium salts of imidazoline, for example those of formula (II)

the quaternary diammonium salts of formula (III);

quaternary ammonium salts containing at least one ester group, such as those of formula (IV).

Preferred quaternary ammonium salts of formula (V) are alkyltrimethylammonium chlorides in which the alkyl radical contains approximately from 12 to 22 carbon atoms, particularly behenyltrimethylammonium chloride (Genamin® KDMP from Clariant) and cetyltrimethylammonium, and palmitylamidopropyltrimethylammonium chloride or stearamidopropyldimethyl(myristyl acetate)ammonium chloride marketed under the name CERAPHYL® 70 by VAN DYK.

The particularly preferred cationic surfactants in the process of the invention are selected from quaternary ammonium salts and in particular from palmitylamidopropyltrimethylammonium chloride, cetyltrimethylammonium chloride and behenyltrimethylammonium chloride.

The compositions according to the invention comprise the fatty compound(s), the non-ionic surfactant(s) and the cationic surfactant(s) in a weight ratio fatty compound(s)/(nonionic surfactant(s)+cationic surfactant(s)) that is generally below 1.5 and preferably between 0.1 and 1.

These compositions are obtainable by the process of the invention such as described above.

The pH of the compositions of the invention is generally between 3 and 8 and preferably between 4 and 7.

The compositions according to the invention can also contain additives such as cationic, anionic, non-ionic or amphoteric polymers, modified or unmodified non-volatile silicones, associative or non-associative, natural or synthetic, anionic, amphoteric, zwitterionic, non-ionic or cationic polymeric thickeners, non-polymeric thickeners such as electrolytes, sugars, pearlescent agents, opacifiers, sun filters, vitamins or provitamins, perfumes, colourants, organic or mineral particles, preservatives and pH stabilizers.

Those skilled in the art will take care to choose any additives and their amount in such a way that they do not detract from the properties of the compositions of the present invention.

These additives are present in the composition according to the invention in an amount ranging from 0 to 50% by weight, based on the total weight of the composition.

The compositions can be used e.g. as cleaning, dyeing or perming compositions or as treatment compositions before or after shampoo, dyeing, perming, bleaching or straightening. Preferably, the compositions of the invention are conditioners.

The present invention further relates to a method of cosmetic treatment of keratin materials which consists in applying an effective amount of a cosmetic composition, such as described above, to the keratin materials and in rinsing, if appropriate, after an optional period of exposure.

The examples which follow illustrate the present invention but must not be considered in any way as implying a limitation.

EXAMPLES

The compositions of Examples 1 to 14 according to the invention are prepared by the procedure of the invention from the ingredients indicated in Tables 1 to, 3 below. Cationic nanoemulsions were ultimately obtained.

TABLE 1

| | Amount in % by weight | | | | |
|---|---|---|---|---|---|
| | Ex. 1 | Ex. 2 | Ex. 3 | Ex. 4 | Ex. 5 |
| Hydrogenated castor oil with 35 EO[1] | 9 | 7.5 | 15 | 11.8 | 9.75 |
| Hydrogenated castor oil with 7 EO[2] | 3 | 2.5 | — | 3.9 | 3.25 |
| Olive oil with 7 EO[3] | — | — | 5 | — | — |
| Isopropyl myristate | 8 | — | — | — | — |
| Isononyl isononanoate | — | — | — | — | 7 |
| Jojoba wax transesterified with ethanol | — | 10 | — | 6.8 | — |
| Jojoba wax | — | — | — | 1.2 | — |
| Olive oil transesterified with hexanol | — | — | 8.6 | — | — |
| Palmitylamidopropyltrimethylammonium chloride[4] | — | — | — | — | 1.5 |
| Cetyltrimethylammonium chloride (AS) | — | — | 2 | — | — |

TABLE 1-continued

| | Amount in % by weight | | | | |
|---|---|---|---|---|---|
| | Ex. 1 | Ex. 2 | Ex. 3 | Ex. 4 | Ex. 5 |
| Behenyltrimethylammonium chloride[5] (AS) | 1.6 | 1.6 | — | 1.4 | — |
| Aminated silicone microemulsion (AS) | — | 1.2 | — | — | — |
| Glycerol | — | — | — | 5 | — |
| Water qs | 100 | 100 | 100 | 100 | 100 |

AS: active substance
[1] sold under the name ARLATONE ® 980 by ICI
[2] sold under the name ARLATONE ® 989 by ICI
[3] sold under the name OLIVEM ® 300 by B&T
[4] sold under the trade name Varisoft ® PATC by WITCO
[5] sold under the trade name Genamin ® KDMP by Clariant GmbH

TABLE 2

| | Amount in % by weight | | | | |
|---|---|---|---|---|---|
| | Ex. 6 | Ex. 7 | Ex. 8 | Ex. 9 | Ex. 10 |
| Sorbitan monooleate with 20 EO[1] | 9.6 | — | — | — | 2.4 |
| Sorbitan monolaurate[2] | 2.4 | — | — | — | — |
| Polyethoxylated oleyl alcohol (10 EO)[3] | — | 10 | 9.6 | — | — |
| Polyethoxylated oleyl alcohol (2 EO)[4] | — | — | 2.4 | — | — |
| Polyethoxylated linear $C_{12}$-$C_{14}$ alcohol (7 EO)[5] | — | — | — | 12 | — |
| Methylglucoside dioleate[6] | — | — | — | — | 9.6 |
| Isopropyl myristate | 8 | 10 | — | 7 | — |
| Isononyl isononanoate | — | — | — | — | 8 |
| Jojoba wax transesterified with ethanol | — | — | 8 | 1 | — |
| Cetyltrimethylammonium chloride (AS) | — | — | 2 | 2 | — |
| Behenyltrimethylammonium chloride[7] (AS) | 1.6 | 1.6 | — | — | 1.5 |
| Aminated silicone microemulsion (AS) | — | 1.2 | — | — | — |
| Water qs | 100 | 100 | 100 | 100 | 100 |

[1] sold under the trade name Tween ® 80 by Uniquema
[2] sold under the trade name Span ® 20 by Uniquema
[3] sold under the trade name Brij ® 96 by Uniquema
[4] sold under the trade name Brij ® 92 by Uniquema
[5] sold under the trade name Synperonic ® L7 by Uniquema
[6] sold under the trade name Glucate ® DO by Amerchol
[7] sold under the trade name Genamin ® KDMP by Clariant GmbH

TABLE 3

| | Amount in % by weight | | | |
|---|---|---|---|---|
| | Ex. 11 | Ex. 12 | Ex. 13 | Ex. 14 |
| Glycerol monostearate (30 EO)[1] | 3.6 | — | — | — |
| Decaglyceryl monooleate[2] | 8.4 | 5 | — | — |
| Sorbitan monooleate with 20 EO[3] | — | 5 | — | — |
| ($C_{12}$-$C_{14}$-alkyl)glycoside[4] | — | — | 1.6 | — |
| Sorbitan monolaurate with 4 EO[5] | — | — | 6.4 | — |
| ($C_8$-$C_{14}$-alkyl)glycoside[6] | — | — | — | 3 |
| Sorbitan monooleate with 5 EO[7] | — | — | — | 7 |
| Isopropyl myristate | 7.5 | — | 12 | 10 |
| Jojoba wax transesterified with ethanol | — | 10 | — | — |
| Jojoba wax | 0.5 | — | — | — |
| Palmitylamidopropyltrimethylammonium chloride[8] | — | — | — | 2 |
| Cetyltrimethylammonium chloride | — | — | 2 | 2 |
| Behenyltrimethylammonium chloride[9] (AS) | 1.6 | 1.6 | — | — |

TABLE 3-continued

| | Amount in % by weight | | | |
|---|---|---|---|---|
| | Ex. 11 | Ex. 12 | Ex. 13 | Ex. 14 |
| Aminated silicone microemulsion (AS) | — | 1.2 | — | — |
| Glycerol | — | — | — | 5 |
| Water qs | 100 | 100 | 100 | 100 |

[1] sold under the trade name Tagat ® S by Goldschmidt
[2] sold under the trade name Decaglyn ® 1-0 by Nikkol
[3] sold under the trade name Tween ® 80 by Uniquema
[4] sold under the trade name Glucopon ® 600 C sup by Cognis
[5] sold under the trade name Tween ® 21 by Uniquema
[6] sold under the trade name Glucopon ® 650 EC/hh sup by Cognis
[7] sold under the trade name Tween ® 81 by Uniquema
[8] sold under the trade name Varisoft ® PATC by WITCO
[9] sold under the trade name Genamin ® KDMP by Clariant GmbH The number-average particle size and the turbidity of the compositions of Examples 1 to 14 were measured by methods such as described above to give the following results:
a number-average particle size strictly below 100 nm, and
a turbidity strictly below 150 NTU.

When applied to hair as conditioners, these compositions give said hair softness, suppleness and smoothness, and tone.

The invention Claimed is:

1. A process for preparing a cationic nanoemulsion, comprising
   (a) mixing, with agitation, at least one fatty compound and at least one non-ionic surfactant at a temperature $T_m$ above the melting point of the at least one fatty compound and the at least one non-ionic surfactant under normal atmospheric pressure, wherein the at least one non-ionic surfactant and the at least one fatty compound are present in amounts suitable to form an oil-in-water emulsion with water;
   (b) adding water, with agitation, to form an oil-in-water nanoemulsion, and
   (c) adding at least one cationic surfactant to the nanoemulsion.

2. The process according to claim 1, wherein the $T_m$ is from about 20°C. to about 100°C.

3. The process according to claim 1, wherein the weight ratio τ of the at least one fatty compound to the at least one non-ionic surfactant is not more than 2.

4. The process according to claim 3, wherein the weight ratio τ of the at least one fatty compound to the at least one non-ionic surfactant is from 0.1 to 1.5.

5. The process according to claim 3, wherein the weight ratio τ of the at least one fatty compound to the at least one non-ionic surfactant is from 0.1 to 1.

6. The process according to claim 1, further comprising cooling the nanoemulsion to about 20°C. before the at least one cationic surfactant is added in (c).

7. The process according to claim 1, further comprising cooling the nanoemulsion to about 20°C. after the at least one cationic surfactant is added in (c).

8. The process according to claim 1, wherein the at least one cationic surfactant is added in the form of an aqueous solution or dispersion.

9. The process according to claim 1, wherein the at least one fatty compound is selected from group consisting of fatty acid esters, transesterified vegetable oils, non-transesterified vegetable oils, and mixtures thereof.

10. The process according to claim 1, wherein the at least one fatty compound is selected from the group consisting of a compound of the formula $R_aCOOR_b$, in which $R_a$ is a radical of a saturated or unsaturated higher fatty acid containing from 6 to 29 carbon atoms and $R_b$ is a saturated or unsaturated hydrocarbon chain containing from 1 to 30 carbon atoms; sweet-almond oil, avocado oil, castor oil, olive oil, jojoba wax, sunflower oil, wheatgerm oil, sesame oil, groundnut oil, grape seed oil, soya oil, colza oil, safflower oil, copra oil, maize oil, hazelnut oil, shea butter, palm oil, apricot kernel oil, calophyllum oil; olive oil transesterified with hexanol, jojoba wax transesterified with ethanol; and mixtures thereof.

11. The process according to claim 10, wherein the at least one fatty compound is a compound of the formula $R_aCOOR_b$ and wherein $R_a$ is a radical of a saturated or unsaturated higher fatty acid containing from 8 to 22 carbon atoms.

12. The process according to claim 10, wherein the at least one fatty compound is a compound of the formula $R_aCOOR_b$ and wherein $R_b$ is a radical of a saturated or unsaturated hydrocarbon chain containing from 1 to 12 carbon atoms 13. The process according to claim 10, wherein the at least one fatty compound is selected from the group consisting of isopropyl myristate, isononyl isononanoate, jojoba wax, olive oil transesterified with hexanol, jojoba wax transesterified with ethanol, and mixtures thereof.

14. The process according to claim 1, wherein at least two non-ionic surfactants are mixed in step (a).

15. The process according to claim 1, wherein the at least one non-ionic surfactant is selected from the group consisting of polyalkoxylated hydrogenated vegetable oils, polyalkoxylated non-hydrogenated vegetable oils, polyalkoxylated hydrogenated $C_{8-30}$ fatty acid monoglycerides, polyalkoxylated non-hydrogenated $C_{8-30}$ fatty acid monoglycerides, polyalkoxylated hydrogenated $C_{8-30}$ fatty acid diglycerides, polyalkoxylated non-hydrogenated $C_{8-30}$ fatty acid diglycerides, polyalkoxylated hydrogenated $C_{8-30}$ fatty acid triglycerides, polyalkoxylated non-hydrogenated $C_{8-30}$ fatty acid triglycerides, polyethoxylated alcohols, polypropoxylated alcohols, polyethoxylated alpha-diols, polypropoxylated alpha-diols, polyethoxylated alkylphenols having a fatty chain, polypropoxylated alkylphenols having a fatty chain, ethylene oxide/propylene oxide copolymers, condensation products of ethylene oxide and propylene oxide with fatty alcohols; polyethoxylated fatty amides having from 2 to 30 mol of ethylene oxide, polyglycerolated fatty amides containing an average of 1 to 5 glycerol groups; fatty acid esters of sorbitan, polyethoxylated fatty acid esters of sorbitan having from 2 to 30 mol of ethylene oxide; fatty acid esters of sucrose, fatty acid esters of polyethylene glycol, $C_{8-30}$ fatty acid esters of polyglycerol, alkylpolyglycosides, N-alkylglucamine derivatives, amine oxides, and mixtures thereof.

16. The process according to claim 15, wherein the at least one non-ionic surfactant is selected from the group consisting of polyalkoxylated hydrogenated vegetable oils containing from 2 to 50 mol of alkylene oxide, polyalkoxylated non-hydrogenated vegetable oils containing from 2 to 50 mol of alkylene oxide, polyalkoxylated hydrogenated $C_{8-30}$ fatty acid monoglycerides containing from 2 to 50 mol of alkylene oxide, polyalkoxylated non-hydrogenated $C_{8-30}$ fatty acid monoglycerides containing from 2 to 50 mol of alkylene oxide, polyalkoxylated hydrogenated $C_{8-30}$ fatty acid diglycerides containing from 2 to 50 mol of alkylene oxide, polyalkoxylated non-hydrogenated $C_{8-30}$ fatty acid diglycerides containing from 2 to 50 mol of alkylene oxide, polyalkoxylated hydrogenated $C_{8-30}$ fatty acid triglycerides containing from 2 to 50 mol of alkylene oxide, polyalkoxylated non-hydrogenated $C_{8-30}$ fatty acid triglycerides containing from 2 to 50 mol of alkylene oxide, polyethoxylated alcohols containing from 2 to 50 ethylene oxide groups, polypropoxylated alcohols containing from 2 to 50 propylene oxide groups, polyethoxylated alpha-diols containing from 2 to 50 ethylene oxide groups, polypropoxylated alpha-diols containing from 2 to 50 propylene oxide groups, polyethoxylated alkylphenols having a fatty chain containing from 2 to 50 ethylene oxide groups, polypropoxylated alkylphenols having a fatty chain containing from 2 to 50 propylene oxide groups, polyglycerolated fatty acid amides containing an average of from 1.5 to 4 glycerol groups, ($C_{10}$-$C_{14}$-alkyl)amine oxides, N-acylaminopropylmorpholine oxides, and mixtures thereof.

17. The process according to claim 15, wherein the at least one non-ionic surfactant is selected from the group consisting of polyethoxylated hydrogenated castor oil with 35 EO, polyethoxylated hydrogenated castor oil with 7 EO, polyethoxylated olive oil with 7 EO, sorbitan monooleates with 4 EO, 5 EO or 20 EO, ($C_{12}$-$C_{14}$-alkyl)glycosides, ($C_8$-$C_{14}$-alkyl)glycosides, glycerol monostearate with 30 EO, decaglyceryl monooleate, polyethoxylated oleyl alcohol with 2 or 10 EO, polyethoxylated lauryl alcohol with 7 EO, methylglucoside dioleate, and mixtures thereof.

18. The process according to claim 1, wherein the cationic surfactant is selected from the group consisting of:
a compound of formula (I):

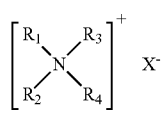

(I)

wherein $R_1$ to $R_4$, which can be identical or different, are a linear or branched aliphatic radical containing from 1 to 30 carbon atoms or an aromatic radical; and X is an anion selected from the group consisting of halides, phosphates, acetates, lactates, alkyl($C_1$-$C_6$)sulphates, ($C_1$-$C_6$-alkyl)sulphonates, and ($C_1$-$C_6$-alkyl)arylsulphonates;

a quaternary ammonium salt of imidazoline;

a quaternary diammonium salt of formula (III):

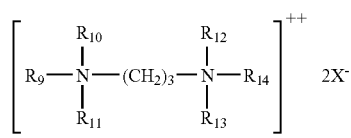

(III)

wherein $R_9$ is an aliphatic radical containing from about 16 to about 30 carbon atoms, $R_{10}$, $R_{11}$, $R_{12}$, $R_{13}$ and $R_{14}$, which are identical or different, are selected from the group consisting of hydrogen and an alkyl radical containing from 1 to 4 carbon atoms; and X is an anion selected from the group consisting of halides, acetates, phosphates, nitrates and methylsulphates; and a quaternary ammonium salt comprising at least one ester group.

19. The process according to claim 18, wherein the cationic surfactants are selected from the group consisting of palmitylamidopropyltrimethylammonium chloride, cetyltrimethylammonium chloride, and behenyltrimethylammonium chloride.

20. The process according to claim 1, wherein the at least one fatty compound is present in an amount of from 1 to 30% by weight based on the total weight of the cationic nanoemulsion.

21. The process according to claim 20, wherein the at least one fatty compound is present in an amount of from 1 to 20% by weight based on the total weight of the cationic nanoemulsion.

22. The process according to claim 1, wherein the at least one non-ionic surfactant is present in an amount of from 2 to 30% by weight based on the total weight of the cationic nanoemulsion.

23. The process according to claim 22, wherein the at least one non-ionic surfactant is present in an amount of from 2 to 20% by weight based on the total weight of the cationic nanoemulsion.

24. The process according to claim 1, wherein the water is present in an amount of from 40 to 97% by weight based on the total weight of the cationic nanoemulsion.

25. The process according to claim 24, wherein the water is present in an amount of from 50 to 90% by weight based on the total weight of the cationic nanoemulsion.

26. The process according to claim 1, wherein the at least one cationic surfactant is present in an amount of from 0.1 to 10% by weight based on the total weight of the cationic nanoemulsion.

27. The process according to claim 26, wherein the at least one cationic surfactant is present in an amount of from 0.2 to 6% by weight based on the total weight of the cationic nanoemulsion.

28. The process according to claim 1, wherein the at least one non-ionic surfactant comprises oxyalkylenation and is present in an amount of from 8 to 20% by weight based on the total weight of the cationic nanoemulsion.

* * * * *

UNITED STATES PATENT AND TRADEMARK OFFICE
CERTIFICATE OF CORRECTION

| | | |
|---|---|---|
| PATENT NO. | : 7,476,393 B2 | Page 1 of 1 |
| APPLICATION NO. | : 10/717626 | |
| DATED | : January 13, 2009 | |
| INVENTOR(S) | : Claude Dubief et al. | |

It is certified that error appears in the above-identified patent and that said Letters Patent is hereby corrected as shown below:

Column 14, line 8, "a quatemary ammonium" should be --a quaternary ammonium--.

Signed and Sealed this

Twenty-third Day of June, 2009

JOHN DOLL
*Acting Director of the United States Patent and Trademark Office*